US00PP26812P3

(12) United States Plant Patent
Ui

(10) Patent No.: US PP26,812 P3
(45) Date of Patent: Jun. 7, 2016

(54) ***CALIBRACHOA* PLANT NAMED 'SAKCAL112'**

(50) Latin Name: ***Calibrachoa* spp.**
Varietal Denomination: SAKCAL112

(71) Applicant: Sakata Seed Corporation, Yokohama (JP)

(72) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 116 days.

(21) Appl. No.: 14/120,066

(22) Filed: Apr. 21, 2014

(65) Prior Publication Data

US 2015/0305222 P1 Oct. 22, 2015

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — June Hwu

(74) *Attorney, Agent, or Firm* — James M. Weatherly; Bethany R. Roahrig; Cochran Freund & Young, LLC

(57) ABSTRACT

A *Calibrachoa* plant particularly distinguished by having a lavender flower color, large flower size and a compact plant growth habit, is disclosed.

1 Drawing Sheet

Genus and species: *Calibrachoa* spp.
Variety denomination: 'SAKCAL112'.

BACKGROUND OF THE NEW PLANT

The present invention comprises a new and distinct variety of *Calibrachoa* plant, botanically known as *Calibrachoa* spp., and referred to by the variety name 'SAKCAL112'. 'SAKCAL112' originated from a hybridization made in 2008 in Kakegawa, Japan. The female parent was the proprietary hybrid *Calibrachoa* breeding line named '7-3B-1A' and had a lavender, pink and rose flower color, large flower size and a mounding plant growth habit. The male parent was the proprietary hybrid *Calibrachoa* breeding line named '7B-16A-1' characterized by its lavender flower color, medium flower size and a compact plant growth habit.

In November 2008, the parental lines '7-3B-1A' and '7B-16A-1' were crossed and 200 seeds were obtained. In February 2009, the $F_1$ seed was sown in the greenhouse, cultivated and plant lines were produced with flower colors of rose, pink and lavender with a mounding and creeping plant growth habit. In May 2009, four plant lines were selected within the $F_1$ plants that had lavender flowers and a compact plant growth habit. In June 2009, the four plant lines were intercrossed and 2,500 seeds were obtained from the group of $F_2$ plants.

In August 2009, 500 seeds were sown in the greenhouse, cultivated and plant lines were produced with flower colors of lavender with a mounding and compact plant growth habit. In November 2009, the line 'K2010-062' was selected for its lavender flower color and compact plant growth habit.

In February 2010, line 'K2010-062' was first vegetatively propagated, cultivated and evaluated. In April 2010, line 'K2010-062' was confirmed to be fixed and stable. In July 2010, line 'K2010-062' was propagated and cultivated again to reconfirm the lines' stability. In November 2010, the line was confirmed to be fixed and stable. The line was subsequently named 'SAKCAL112' and its unique characteristics were found to reproduce true to type in successive generations of asexual propagation via vegetative cuttings in Salinas, Calif. Asexual propagation was performed via excising the terminal 1.0 inches to 1.5 inches of an actively growing stem of the variety.

SUMMARY

The following are the most outstanding and distinguishing characteristics of this new variety when grown under normal horticultural practices in Salinas, Calif.

1. Lavender flower color;
2. Compact growth habit; and
3. Large flower size.

DESCRIPTION OF THE PHOTOGRAPHS

This *Calibrachoa* plant is illustrated by the accompanying photographs which show the plant's overall plant habit including form, foliage, and flowers. The photographs are of a four-month-old plant grown in Salinas, Calif. under greenhouse conditions in the summer of 2013. The colors shown are as true as can be reasonably obtained by conventional photographic procedures.

DESCRIPTION OF THE NEW VARIETY

Figure 1:
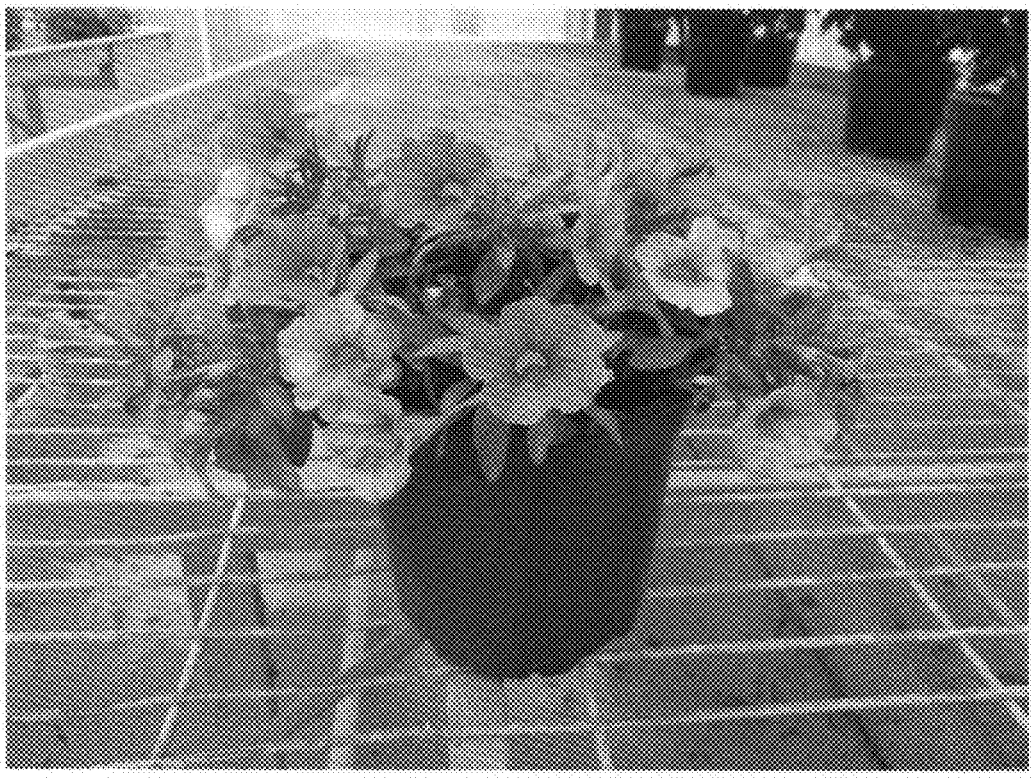
FIG. 1 shows the overall plant habit of the plant grown in a pot.
Figure 2:
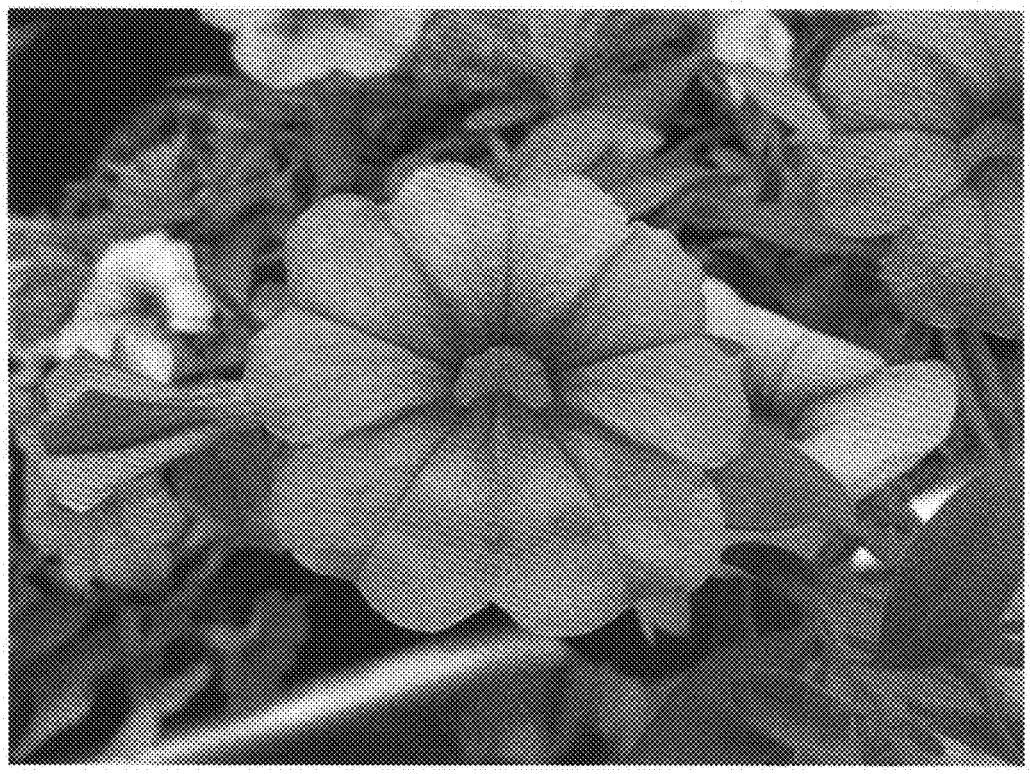
FIG. 2 shows a close-up of the mature inflorescence of the plant.

The following detailed descriptions set forth the distinctive characteristics of 'SAKCAL112'. The data which define these characteristics were collected from asexual reproductions carried out in Salinas, Calif. Data was collected on four-month-old plants grown under greenhouse conditions in Salinas, Calif. in the summer of 2013. Color references are to The R.H.S. Colour Chart of The Royal Horticultural Society of London (R.H.S.), 4th edition (2001).

Classification:

*Family*.—Solanaceae.

*Botanical*.—*Calibrachoa* spp.

*Common*.—*Calibrachoa*.

*Designation*.—'SAKCAL112'.

Parentage:

*Female parent*.—Proprietary hybrid *Calibrachoa* line '7-3B-1A' (unpatented).

*Male parent*.—Proprietary hybrid *Calibrachoa* line '7B-16A-1' (unpatented).

Growth:

*Time to produce a rooted cutting*.—About 4 weeks.

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20-cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form*.—Compact and branching.

*Life cycle*.—Tender perennial.

*Height* (*from soil line to top of foliage*).—7.3 cm.

*Spread*.—24.0 cm.

*Flowering requirements*.—Will flower so long as day length is greater than 12 hours and temperature is above 13° C.

*Temperature tolerances*.—Excellent resistance to rain, heat, and drought. Plants will not tolerate temperatures below 10° C.

Stems:

*General description*.—Circular in cross-section; dull in appearance.

*Stem length*.—8.3 cm.

*Diameter*.—0.2 cm.

*Internode length* (*average*).—2.0 cm.

*Color*.—RHS 144B (Green).

*Pubescence*.—Slight; pubescence is RHS 155C (White).

*Anthocyanin color*.—Absent.

Leaves:

*Arrangement*.—Alternate.

*Shape*.—Elliptic.

*Apex*.—Obtuse.

*Base*.—Attenuate.

*Margin*.—Entire.

*Surface appearance* (*both surfaces*).—Dull.

*Surface pubescence* (*both surfaces*).—Slightly pubescent; pubescence is RHS N155C (White).

*Length*.—3.2 cm.

*Width*.—1.2 cm.

*Color*.—Upper surface: RHS 137A (Yellow-Green). Lower surface: RHS 137C (Yellow-Green).

*Venation*.—Pinnate.

*Petiole*.—Absent; decurrent leaf attachment.

*Fragrance*.—Absent.

Inflorescence:

*Inflorescence type*.—Solitary.

*Flowering habit*.—Indeterminate.

*Time to bloom from propagation*.—10 weeks.

*Total number of flowers*.—Approximately 50.

*Lastingness of individual blooms on the plant*.—5 days.

*Fragrance*.—Absent.

Flower bud:

*Surface texture*.—Pubescent.

*Length*.—2.0 cm.

*Diameter*.—0.5 cm.

*Shape*.—Ovate.

*Color*.—RHS 85A (Violet).

Peduncle:

*Length*.—0.9 cm.

*Diameter*.—0.1 cm.

*Color*.—RHS 145A (Yellow-Green).

*Surface appearance and texture*.—Dull with heavy pubescence; pubescence color is RHS N155C (White).

Corolla:

*Shape*.—Composed of five, fused petals to create a funnel-shaped flower with five fissures and a shallow, yet prominent, indentation of the petal tip at the midvein.

*Flower diameter*.—3.5 cm.

*Flower depth*.—0.5 cm.

*Petals*.—Shape: Obcordate. Apex: Emarginate. Base: Fused. Margin: Entire. Surface texture (both surfaces): Glabrous. Degree of lobing: Strong. Length: 2.7 cm. Width: 1.5 cm. Color: Upper surface: Closest to RHS N82B. Lower surface: Closest to RHS N82C (Purple-Violet).

*Corolla tube*.—Length: 1.5 cm. Diameter: 0.5 cm. Color: Inner surface: RHS 5A (Yellow). Outer surface: Closest to RHS 4B (Yellow) with RHS 79A (Purple) veins.

Calyx:

*Arrangement*.—Composed of 5 sepals, free.

*Sepals*.—Shape: Elliptical. Apex: Obtuse. Margin: Entire. Color (both surfaces): RHS 137A (Green). Length: 1.0 cm. Diameter: 0.2 cm.

Reproductive organs:

*Stamen number*.—5.

*Stamen color*.—RHS 4B (Yellow).

*Stamen form*.—Free.

*Stamen length*.—1.0 cm.

*Pollen color*.—RHS 15A (Yellow).

*Pollen amount*.—Abundant.

*Ovary*.—Superior.

*Placental arrangement*.—Central.

*Pistil number*.—1 (per inflorescence).

*Pistil length*.—0.9 cm.

*Pistil color*.—RHS 154C (Yellow-Green).

*Stigma color*.—RHS 154C (Yellow-Green).

*Stigma length*.—0.1 cm.

*Style length*.—0.8 cm.

*Style color*.—RHS 145C (Yellow-Green).

*Seed production*.—Absent.

*Fruit production*.—Absent.

Disease and insect resistance: Plants are susceptible to *Botrytis*, powdery mildew, various stem and root rots, and certain viruses, such as Tobacco Mosaic Virus and Impatiens Necrotic Spotted Virus. Plants can be infested with aphids, leafminers, whitefly, and various *Lepidoptera*.

COMPARISON WITH PARENTAL LINES AND KNOWN VARIETY

'SAKCAL112' is a new and unique variety of *Calibrachoa* owing to its lavender flower color, large flower size and compact plant growth habit. 'SAKCAL112' is distinguished from its parents as shown in Table 1 below:

TABLE 1

Comparison with Parental Lines

| Characteristic | 'SAKCAL112' | Female parent: '7-3B-1A' | Male parent: '7B-16A-1' |
|---|---|---|---|
| Flower color | Lavender | Lavender, Pink & Rose | Lavender |
| Flower size | Large | Large | Medium |
| Plant growth habit | Compact | Mounding | Compact |

'SAKCAL112' is a new and unique variety of *Calibrachoa* owing to its lavender flower color, compact growth habit and a large flower size. 'SAKCAL112' is most similar to the commercial *Calibrachoa* variety 'SAKCAL106' (U.S. Plant patent application Ser. No. 13/815,966 filed Mar. 19, 2013, abandoned), commercially known as Calipetite® 'Blue'; however there are differences as described in Table 2 below.

TABLE 2

Comparison with Similar Variety

| Characteristic | 'SAKCAL112' | 'SAKCAL106' |
|---|---|---|
| Flower petal color, upper surface | RHS N82B | RHS 83B (Purple) with RHS 77A (Purple) veins and RHS N77A (Purple) at midvein |
| Flower petal color, lower surface | RHS N82C (Purple-Violet) | RHS 83C (Purple) with RHS 77A (Purple) veins and RHS N77A (Purple) at midvein |
| Flower size (diameter) | 3.5 cm | 2.0 cm |

I claim:

1. A new and distinct variety of *Calibrachoa* plant as illustrated and described herein.

* * * * *